United States Patent
Hammarberg

Patent Number: 5,834,629
Date of Patent: Nov. 10, 1998

[54] COMBUSTION SENSOR AND COMBUSTION ENGINE EQUIPPED WITH SUCH A SENSOR

[75] Inventor: Göran Hammarberg, Nykvarn, Sweden

[73] Assignee: Scania CV Aktiebolag, Sodertalje, Sweden

[21] Appl. No.: 391,234

[22] Filed: Feb. 21, 1995

[30] Foreign Application Priority Data

Feb. 22, 1994 [SE] Sweden ................................ 9400603

[51] Int. Cl.⁶ .................................................. G01M 15/00
[52] U.S. Cl. ........................................ 73/35.08; 73/119 A
[58] Field of Search ............................. 73/351, 113, 116, 73/117.3, 119 A, 35.08

[56] References Cited

U.S. PATENT DOCUMENTS

| | | | |
|---|---|---|---|
| 4,036,050 | 7/1977 | Dooley et al. | |
| 4,232,545 | 11/1980 | Dobler et al. | |
| 4,337,648 | 7/1982 | Gillespie | 73/117.3 |
| 4,359,893 | 11/1982 | Kizler et al. | 73/35.08 |
| 4,429,570 | 2/1984 | Tinder | |
| 4,441,021 | 4/1984 | Olson et al. | 73/117.3 |
| 4,444,049 | 4/1984 | Hitchcock | 73/117.3 |
| 4,452,072 | 6/1984 | Damson et al. | 73/116 |
| 4,461,170 | 7/1984 | Suzuki et al. | |
| 4,463,729 | 8/1984 | Bullis et al. | 73/117.3 |
| 4,493,208 | 1/1985 | Grover | 73/117.3 |
| 4,545,238 | 10/1985 | Kinoshita et al. | 73/117.3 |
| 4,643,022 | 2/1987 | Werlberger et al. | 73/117.3 |
| 4,648,266 | 3/1987 | Ikeda | 73/117.3 |
| 4,665,740 | 5/1987 | Matsumoto et al. | 73/116 |
| 4,802,369 | 2/1989 | Morii | 73/116 |
| 4,825,689 | 5/1989 | Haworth et al. | 73/116 |
| 4,887,574 | 12/1989 | Kuroiwa et al. | 73/116 |
| 4,919,099 | 4/1990 | Extance et al. | 73/116 |
| 4,987,771 | 1/1991 | Iwata | 73/117.3 |
| 5,099,683 | 3/1992 | Remboski, Jr. et al. | 73/116 |
| 5,103,789 | 4/1992 | Hartman et al. | 73/116 |
| 5,194,813 | 3/1993 | Hannah et al. | 73/117.3 |

FOREIGN PATENT DOCUMENTS 2211244  6/1989  United Kingdom.
8903520  4/1989  WIPO.

*Primary Examiner*—Richard Chilcot
*Assistant Examiner*—Eric S. McCall
*Attorney, Agent, or Firm*—Ostrolenk, Faber, Gerb & Soffen, LLP

[57] ABSTRACT

The invention relates to a sensor 9 for detecting the degree of ionisation in a combustion chamber 2 in combustion engines with direct injection, and to a combustion engine equipped with such a sensor. The sensor is arranged around and preferably concentrically to the injector 6 in the latter's duct 5 in the cylinder head 1. The measuring electrode of the sensor 9 is substantially sleeve-shaped and is clamped firmly and centered by electrically insulating washers 11, 12 between a shoulder 7 in the duct 5 and a corresponding shoulder on the injector 6. The result is an inexpensive sensor which may easily be replaced without major modifications of the cylinder head or simultaneous replacement of the injector.

13 Claims, 2 Drawing Sheets

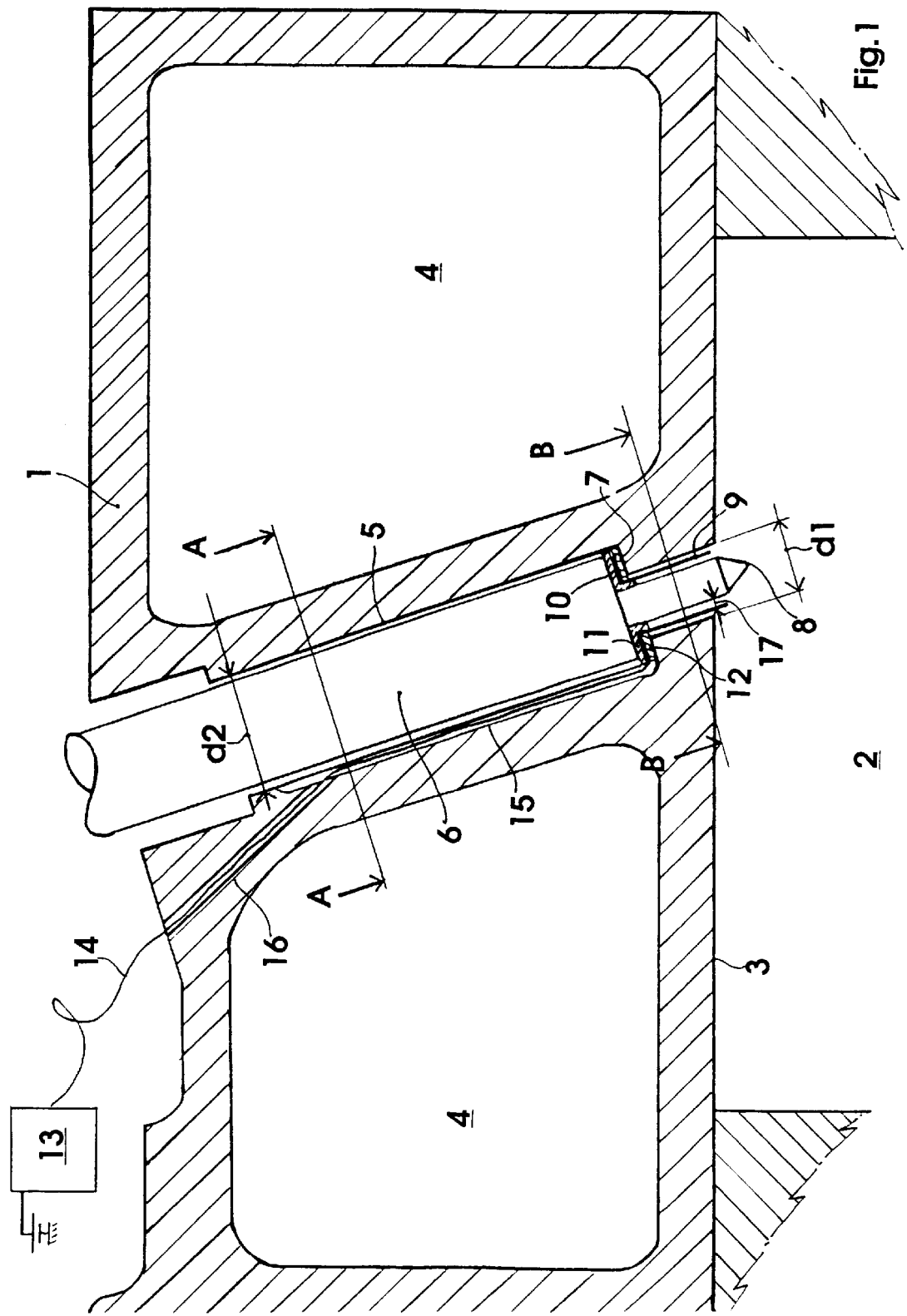

COMBUSTION SENSOR AND COMBUSTION ENGINE EQUIPPED WITH SUCH A SENSOR

BACKGROUND OF THE INVENTION

The present invention relates to a sensor for monitoring the combustion pattern by detecting the degree of ionisation in the combustion chamber of combustion engines and to a combustion engine equipped with such a sensor.

There are a number of existing solutions for incorporating ionisation sensors in combustion engines.

DE,A,4132285 specifies a sensor for detecting the ionisation current in spark-ignition engines whereby the ionic-current detecting electrode of the sensor is incorporated in a spark plug. This obviates the need to have a special hole for the sensor but does require a complicated and expensive spark plug.

U.S. Pat. No. 4,739,731 specifies a sensor for diesel engines which is incorporated in a modified glow plug. This likewise requires no new holes for the sensor if the engine is provided with a glow plug, but the glow plug becomes complicated and expensive.

EP,A,387266 specifies a sensor which is incorporated in the cylinder head gasket by a five-layered sandwich technique.

SUMMARY OF THE INVENTION

One object of the invention is to obviate the creation of new holes into the combustion chamber and to minimise costs pertaining to the sensor. The incorporation of ionic-current sensors in cylinder head gaskets, spark plugs or glow plugs always makes these respective components more expensive.

Another object is to facilitate the replacement of faulty ionic-current sensors without having to replace other important components such as cylinder head gaskets, spark plugs or glow plugs. Other important components may thus be replaced only when these respective components need replacing, thereby further reducing servicing costs.

In this respect the sensor according to the invention includes a substantially sleeve-shaped electrode arranged around an injector for injecting fuel into the combustion chamber, the electrode being in communication with the combustion chamber.

BRIEF DESCRIPTION OF THE DRAWINGS

Other features and advantages of the present invention will become apparent from the following description of the invention which refers to the accompanying drawings.

FIG. 1 shows a schematic cross-section of a cylinder head for a combustion engine with an ionic-current sensor fitted concentrically with a fuel injector.

Figure 3:
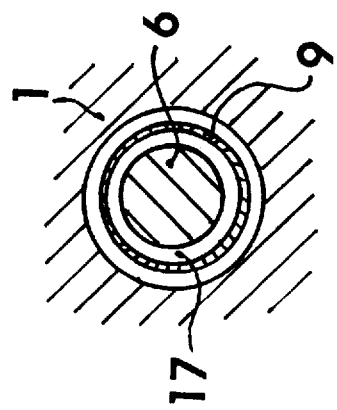
FIG. 3 shows an enlarged view at section B—B in FIG. 1.

DESCRIPTION OF THE PREFERRED EMBODIMENT(S).

FIG. 1 depicts in cross-section a cylinder head 1 with cooling water ducts 4 for a diesel engine and with a lower boundary surface 3 which delineates a combustion chamber 2. An injector 6 for fuel is fitted in a preferably drilled duct 5 through the cylinder head 1. The duct 5 has adjacent to the combustion chamber a first diameter d1 which at a distance from the combustion chamber 2 is smaller than the diameter d2 of the drilled hole, resulting in the formation of a shoulder 7 in the duct. The part of the injector adjacent to the combustion chamber correspondingly has a smaller diameter and conventionally has at its end an injection outlet which in a usual manner incorporates a number of small spray holes. The upper part of the injector has a larger diameter. The shoulder formed on the injector by the diameter change abuts against the shoulder 7 formed in the drilled hole, thereby obtaining positioning of the tip 8 of the injection outlet in the combustion chamber. The injector is conventionally pressed with sealing contact against the shoulder 7 by undepicted fastening devices and is sealed with respect to the duct 5 by sealing rings. In the diagram the gap between the injector and the duct is enlarged so as to make it easier to discern the atomiser 6 and the duct 5.

The sensor for detecting the degree of ionisation in the combustion chamber consists of a substantially sleeve-shaped electrode 9, hereinafter called sleeve, made of an electrically conducting material, and is arranged at least partly enclosing and largely concentrically with the injector 6. The sleeve 9 is shown in FIG. 1 in bold cross-section. The sleeve 9 is positioned and held in place by a bent-out collar-shaped retaining section 10 on the upper end of the sleeve being held between the injector 6 and the shoulder 7 formed in the drilled hole. The retaining section is electrically insulated from the injector and the adjacent wall portions, preferably by washers 11, 12 which are respectively placed above and below the retaining section. The washers 11,12 are made of a heat-resistant electrically insulating material, preferably a TEFLON material or insulating ceramics. The upper washer 11 is a flat washer which cooperates with an axial sleeve-shaped section which it may be advantageous to incorporate with the upper washer. The inside diameter and outside diameter of the upper washer 11 correspond respectively to the outside diameter of the injector and the second diameter d2 of the drilled hole, and the inside diameter and outside diameter of its sleeve-shaped section correspond respectively to the outside diameter of the injector and the inside diameter of the sleeve 9. The lower washer 12 is a simple flat washer, the inside diameter and outside diameter of which correspond respectively to the outside diameter of the sleeve and the second diameter d2 of the drilled hole. This design results in the upper washer 11 by the sleeve 9 being centered about the injector 6, since the sleeve-shaped section of the upper washer 11 acts as a spacer between the injector and the sleeve 9. The sleeve-shaped section of the upper washer 11 is provided with a suitable axial extent which is required for ensuring centering of the sleeve 9, and its length over the lower part of the injector is shorter by a good 50% than the length of the injector 6 from its shoulder. This results in the formation of a radial air gap between the sleeve 9 and the lower part of the injector which is inserted into the combustion chamber 2. This makes it easier to separate the sensor from the injector so that if the sensor becomes faulty it can be replaced without having to replace the injector.

Figure 2:
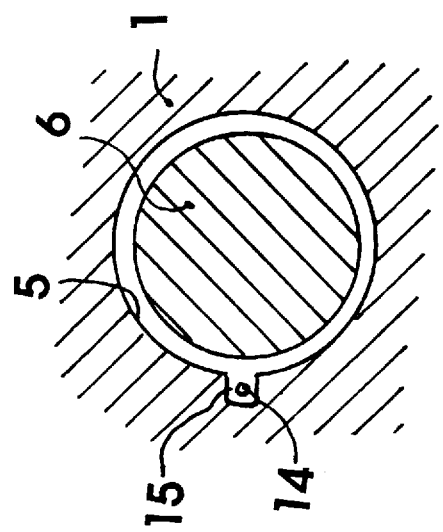
FIG. 2 shows an enlarged view at section A—A in FIG. 1.

The electrode part of the sensor, the sleeve 9, is connected to a detection circuit 13 by means of at least one insulated electrical conductor 14 which is electrically connected to the sleeve 9 and the detection circuit. The electrical conductor is electrically insulated from adjacent wall portions and runs in a recess 15 which is milled out along the upper part of the drilled hole 5. FIG. 2 shows the recess 15 milled out in the drilled hole 5, with the electrical conductor 14 arranged in it.

In a similar manner the electrical conductor is led on through the cylinder head via an oblique drilled hole 16 connecting with the milled-out recess 15. The electrical conductor 14 may also advantageously be incorporated separately in the injector (not depicted), which also means that the electrical conductor may be fastened to the injector with simultaneous electrical insulation with respect to the injector and adjacent parts of the cylinder head. This also means that the detection circuit may be attached to the injector so as to create an easy-to-fit combined injector-and-sensor unit. Such a unit may cooperate with an electronic system controlling the engine.

The sensor with its electrode 9 directed towards to the combustion chamber extends with respect to the combustion chamber 2 to at least level with the lower boundary surface 3 of the cylinder head and ends at a distance from a plane which runs transverse to the longitudinal axis of the injector and through the tip 8 of the injector.

A measuring voltage imposed on the sleeve 9 will therefore supply a current to the adjacent earthed parts of the engine, either to the injector via the air gap 17 or to the cylinder head 1, depending on the degree of ionisation of the gas mixture in the combustion chamber 2, thereby making it possible to monitor the combustion pattern. Via the detection circuit and its cooperation with a fuel injection control system it is then possible in a manner known per se for the injection of fuel to be controlled via electrically influenceable devices with the object of achieving optimum combustion from preferably fuel-economy and emission points of view. The lower end part of the sleeve 9 ends above or level with the position of the spray holes in the tip of the injector so that the injection pattern, i.e. the direction and volume of the fuel sprayed out, is not affected. It may nevertheless be advantageous for the end part of the sleeve to be situated up inside the duct 5 at an axial distance from the plane where the duct 5 opens into the combustion chamber. By making that distance at least as great as the distance 17, the degree of ionisation of a relatively well-defined gas mixture protected from interference can be detected, subject to the sensor signal being stable and representative.

FIG. 3 shows the sleeve 9 arranged concentrically about the lower part of the injector 6 and spaced by the air gap 17.

The electrode 9 does of course not have to take the form of a totally cylindrical sleeve with unified casing surface. The sleeve may be made with cavities or slits etc. The intermediate portion of the sleeve between the collar-shaped retaining section 10 and the end part of the sleeve may take the form of two, three or more slats running axially, preferably distributed evenly over the circumference of the sleeve, which electrically connect the retaining section and the end part of the sleeve. Such slats may thus only occupy one or more parts of the casing-shaped intermediate portion of the sleeve. The end part of the sleeve may be connected to one or more slats and consist of a complete circle or parts of circle segments on the end portion of the sleeve. Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:

1. A sensor for detecting a degree of ionization in a combustion chamber of a combustion engine, which combustion chamber is partly bounded by a cylinder head having a duct which opens into the chamber and in which a fuel injector for injecting fuel directly into the combustion chamber is arranged, the sensor comprising: a substantially sleeve-shaped electrode arranged in the duct surrounding the fuel injector, the electrode being in communication with the combustion chamber and means connected to the electrode for detecting the degree of ionization in the combustion chamber.

2. A sensor according to claim 1, wherein the electrode is structured and arranged relative to the injector such that the electrode is removable from the duct separately from the injector.

3. A sensor according to claim 1, wherein the electrode is disposed concentrically around the injector.

4. A sensor according to claim 3, wherein the electrode is electrically conducting and further comprising a plurality of insulators for electrically insulating the electrode from the injector and adjacent wall portions of the duct.

5. A sensor according to claim 4, wherein the duct adjacent to the combustion chamber has a first diameter (d1) which is smaller than a duct diameter (d2) at a distance from the combustion chamber so as to form a first shoulder and the injector has a corresponding second shoulder which abuts the first shoulder and wherein the electrode is provided with a retaining section which is held between the injector and the first shoulder.

6. A sensor according to claim 5, wherein the retaining section is collar-shaped.

7. A sensor according to claim 5, further including an axial sleeve-shaped insulating member for centering the electrode about the injector.

8. A sensor according to claim 7, wherein the axial sleeve-shaped member is an integral part of one of the plurality of insulators.

9. A sensor according to claim 7, wherein the electrode is centered about the injector such that an insulating air gap is formed between the electrode and a part of the injector adjacent to the combustion chamber, and a corresponding air gap is formed between the electrode and adjacent wall portions of the duct.

10. A sensor according to claim 9, wherein the detection means includes a detection circuit electrically connected to the electrode.

11. A sensor according to claim 10, wherein at least one electrical conductor, electrically insulated from the cylinder head, is provided for connecting the detection circuit to the electrode.

12. A combustion engine having means for detecting a degree of ionization in a combustion chamber of the engine, which comprises:

a cylinder head which partly bounds the combustion chamber;

a fuel injector arranged in a duct which runs through the cylinder head for injecting fuel directly into the combustion chamber;

a substantially sleeve-shaped sensor disposed in the duct surrounding the injector, the sensor being in communication with a fuel-air mixture contained in the combustion chamber;

a plurality of insulators for electrically insulating the sensor from the injector and adjacent wall portions of the duct; and a detection circuit electrically connected to the sensor for detecting a degree of ionization in the combustion chamber.

13. A combustion engine according to claim 12, wherein the duct is provided with an axial recess and wherein at least one electrical conductor is disposed in the recess, the conductor being insulated from adjacent wall portions of the recess and being connected electrically to the electrode and the detection circuit.

* * * * *